United States Patent [19]

Frank

[11] 4,162,542
[45] Jul. 31, 1979

[54] EYE PROTECTORS

[76] Inventor: Jerome M. Frank, 10549 Valparaisa St., Los Angeles, Calif. 90034

[21] Appl. No.: 795,180

[22] Filed: May 9, 1977

[51] Int. Cl.² ............................................. A61F 9/02
[52] U.S. Cl. ............................................. 2/15; 2/430; 2/440; 2/446
[58] Field of Search ............... 2/445, 446, 452, 432, 2/433, 15, 12, 430; 351/44, 45, 126, 128, 124

[56] References Cited

U.S. PATENT DOCUMENTS

| | | |
|---|---|---|
| 583,590 | 6/1897 | Bennett ............................ 2/452 X |
| 1,291,433 | 1/1919 | Day ................................. 351/124 |
| 1,686,848 | 10/1928 | Fowler ............................. 2/433 |
| 1,838,646 | 12/1931 | Walsh, Jr. ....................... 2/445 X |
| 2,510,539 | 6/1950 | Arbenz ........................... 2/432 |
| 2,680,847 | 6/1954 | Ball ................................. 2/446 |
| 2,844,994 | 7/1958 | Filler .............................. 2/432 X |
| 3,020,552 | 2/1962 | Coon .............................. 2/15 |
| 3,394,980 | 7/1968 | Dym ............................... 2/446 X |
| 3,605,116 | 9/1971 | Simpson ......................... 2/445 |
| 4,051,557 | 10/1977 | Bengtson et al. ............... 2/430 |

FOREIGN PATENT DOCUMENTS 2514439 10/1976 Fed. Rep. of Germany .............. 2/432
684750 3/1930 France .............................. 2/433
1393280 2/1965 France .............................. 2/15

Primary Examiner—Peter Nerbun
Attorney, Agent, or Firm—Blakely, Sokoloff, Taylor & Zafman

[57] ABSTRACT

The improved eye protectors of the present invention comprise a pair of eye cups, and a transparent readily heat remoldable bridge releasably connected to the cups. The bridge can be shaped to fit nose bridges of various sizes and shapes, and can be regulated to adjust the spacing of the cups to accommodate various eye distances. The cups are generally hemispherical and either opaque or transparent and tinted to protect the eyes from both sun and wind. One form of eye cup is cut away on a lower portion to form a sun shade over the eye, or upon reversal, to form a mini eye protector. Another form of the protector is transparent, has a head strap for use by skiers, etc., as a form of goggles. The protectors are simple, inexpensive and durable, with a variety of novel characteristics and uses, providing various forms of eye shading and protection while allowing tanning through the nose bridge and the head strap. Metallic plating of the cups keeps the cups cool when used in the direct sun.

18 Claims, 15 Drawing Figures

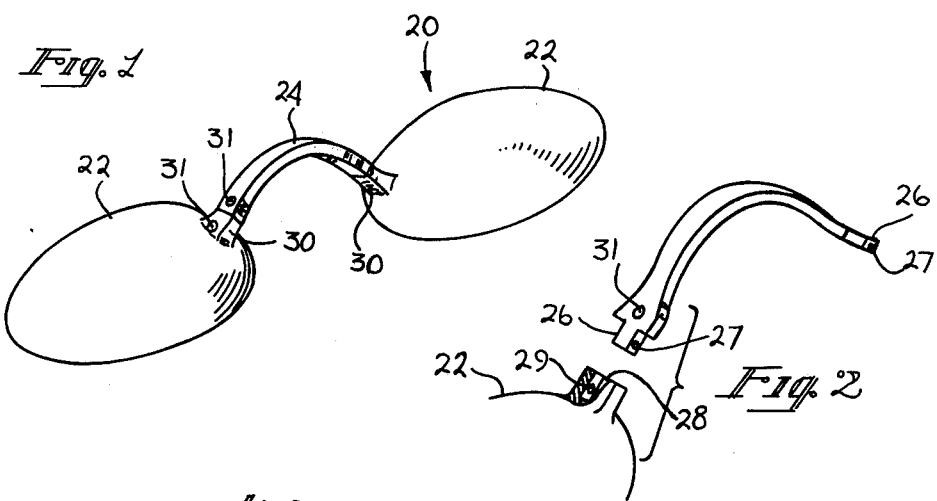
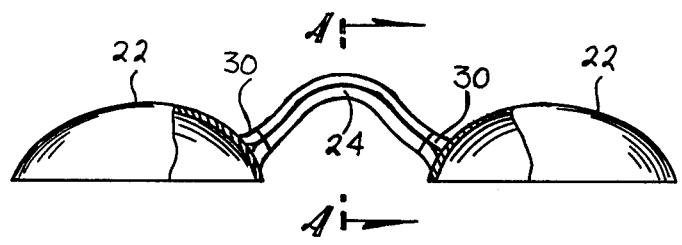
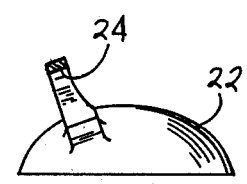
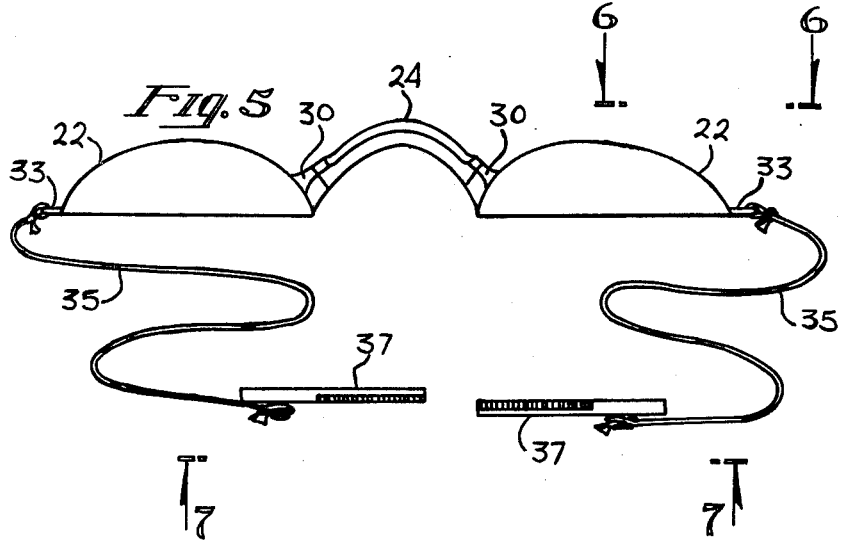
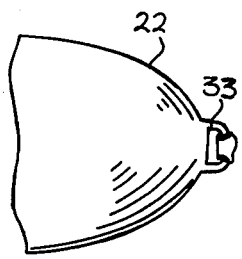
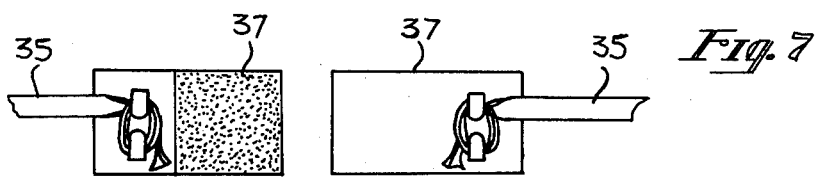
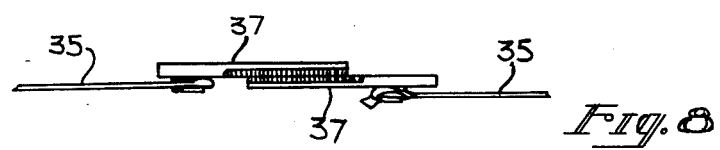

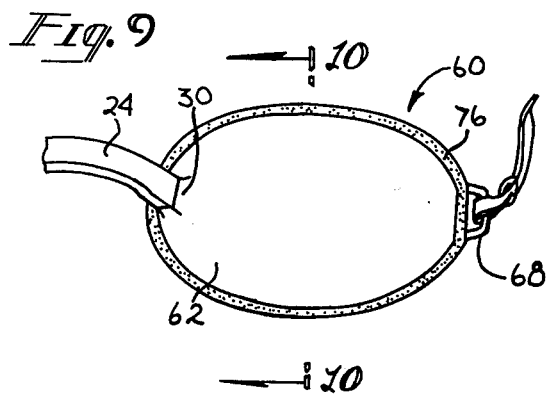
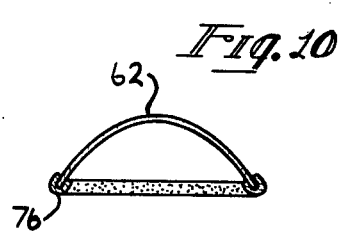
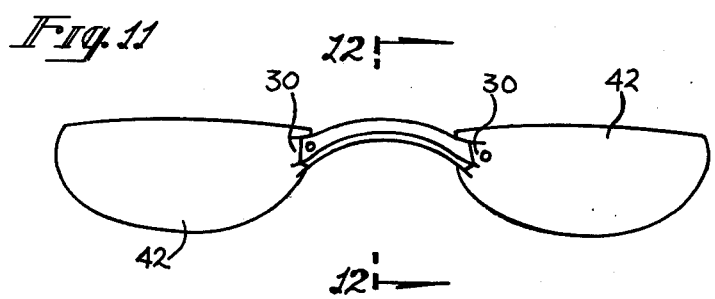
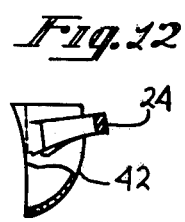
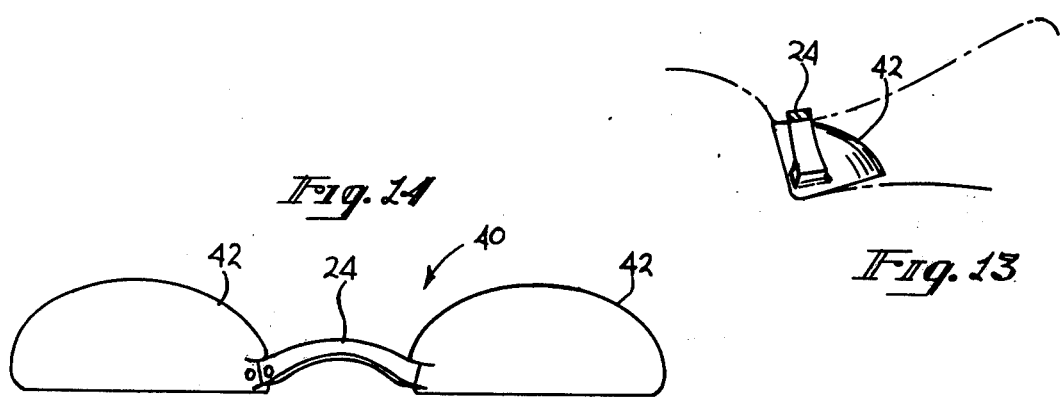
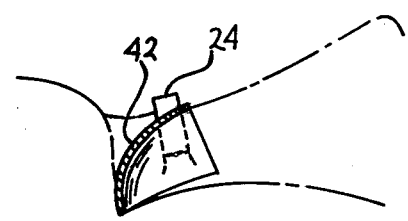

EYE PROTECTORS

BACKGROUND OF THE INVENTION

1. Field of the Invention

The present invention generally relates to eye accessories, and more particularly to improved means of protecting the eyes against wind and sun.

2. Description of the Prior Art

The present invention is primarily intended for use as an eye protector for sunbathers, though alternatively it may also be used as a form of goggles for skiers and the like, or even tinted somewhat to be used as a form of sunglasses. Accordingly only the prior art relating to these primary uses is described herein.

Eye protectors for use by sunbathers are well known in the prior art. Generally speaking such protectors are one piece molded members having a pair of eye cups separated by an integral nose bridge. The eye cups are proportioned to fit over the eyelids to cover the entire eyeball so as to shade the eye, thereby protecting the eyeball and avoiding burning of the eyelids. However, since the eye cups must necessarily be opaque to achieve this purpose, the bridge is also opaque, preventing tanning thereunder, so as to create an undesirable white mark across the nose of the sunbather. In general such devices are not adjustable, and are available only with the full eye cups as described.

Goggles as commonly worn by skiers and the like generally are relatively large eye protection devices covering a substantial region of the head in the area of the eyes so as to block the sun therefrom, resulting in peculiar tanning patterns on the wearers face. Further, the straps or other devices used to retain the goggles in position themselves normally block the sun's rays, creating untanned lines or streaks extending rearward to the hairlines. Of course similar comments are also applicable to conventional sunglasses, because of their size and substantial opaque regions.

Finally the only form of eyeshades well known in the prior art is the conventional visor, shading not only the eyes but generally the entire forehead and nose, contrary to the objectives of a typical sunbather.

BRIEF SUMMARY OF THE INVENTION

The improved eye protectors of the present invention comprise a pair of eye cups and a transparent readily heat remoldable bridge or strap releasably connected to the cups. The bridge can be shaped to fit nose bridges of various sizes and shapes, and can be regulated to adjust the spacing of the cups to accommodate various eye distances. The cups are generally hemispherical and either opaque or transparent and tinted to protect the eyes from both sun and wind. One form of eye cup is cut away on a lower portion to form a sun shade over the eye, or upon reversal, to form a mini eye protector. Another form of the protector is transparent, has an air sealing cushion along the periphery of each cup, and has a head strap for use by skiers, etc., as a form of goggles. The protectors are simple, inexpensive and durable, with a variety of novel characteristics and uses, providing various forms of eye shading and protection while allowing tanning through the nose bridge and the head strap. Separability of the bridge and eye cups provides maximum flexibility in configuration, disposition and decoration of the eye cups without interference with the transparency of the bridge. Metallic plating may be used on the cups to reflect the sun's rays, thereby achieving the desired objective while avoiding heating of the eye cups.

BRIEF DESCRIPTION OF THE DRAWINGS

FIG. 1 is a perspective view of the embodiment of the eye protectors of the present invention.

FIG. 2 is a partial cross-sectional view of a portion of FIG. 1 illustrating the coupling of the nose bridge to the eye cups.

FIG. 3 is a plan view, partially cut away, of the eye protectors of FIG. 1.

FIG. 4 is a slide plan view in cross-section.

FIG. 5 is a top plan view of an alternate embodiment.

FIG. 6 is a front view of a portion of the embodiment of FIG. 5.

FIGS. 7 and 8 are views illustrating one form of fastener for the head strap of the alternate embodiment.

FIGS. 9 and 10 illustrate a still further alternate embodiment for use as goggles.

FIGS. 11, 12 and 13 illustrate a still further alternate embodiment for use as mini eye protectors.

FIGS. 14 and 15 illustrate the use of the embodiment of FIGS. 11 through 14 as eye shades.

DETAILED DESCRIPTION OF THE INVENTION

First referring to FIG. 1, one embodiment of the present invention improved eye protector may be seen. Individual eye protectors 20 each comprise a pair of generally hemispherical (see also FIGS. 3 and 4) eye cups 22 releasably connected together through a transparent bridge 24. As seen particularly in FIG. 2, bridge 24 includes tabs 26 on opposite ends thereof, which tabs 26 are of reduced width and each is releasably slidably received within a suitably shaped pocket 28 in an extension 30 on an eye cup 22. Tabs 26 may be held in pockets 28 by frictional engagement, with locking buttons 27 on tabs 26 being received in depressions 29 in pockets 28 to provide a detent in the assembled state. In the preferred embodiment, raised regions 31 are also provided on one side of the nose bridge and on one of the cups 22 to indicate the proper assembly orientation of the parts.

It will be noted that each eye cup 22 is in reality somewhat egg-shaped in outline, and is adapted to fit against the sides of the head, the side of the nose, and the skin above and below the eyes, when worn, as well as in front of the eye, so as to fully protect the eye against the sun. Each cup 22 may be opaque for sunbathing, or as an alternative, may be relatively transparent and subsequently rendered opaque by vapor plating, etc., to provide a highly functional and highly decorative device. (Actually, plating is preferred, as the reflectivity achieved provides the light blockage desired while allowing the eye cups to remain cool and unheated by the sun). Obviously, even decorative decals may be placed over the cup for further decoration. Cups 29 preferably are made of resilient plastic material, such as a thermoplastic, for example, polymethyl methacrylate, polystyrene, polyethylene, or polyvinyl resins of various types or any suitable clear thermosetting plastic, polyesters, etc.

Using a three piece assembly allows bridge 24 to be transparent, so that a white line is not left on the nose during suntanning. Also light focusing tendencies of the bridge are avoided by using a rectangular cross-section member. Using a thermoplastic, it is also readily heat remoldable or deformable so that it can be reshaped in hot water to fully conform to the particular size and shape of the nose upon which it is to be supported, and to adjust the position and spacing of eye cups 22 to conform to individual requirements. Bridge 24 is formed of any suitable thermoplastic material, such as those specified above for cups 22, provided that the particular plastic selected can be heat deformed at low temperature, for example, in hot water or the like.

Protectors 20 are normally worn in the prone position (sunbathing, etc.), but can be fitted with head straps for wearing while walking, etc., as shown in FIGS. 5 through 8. In this case, each eye cup 22 is provided with an integral loop 33 at the outer extremity thereof so that a clear plastic rectangular strap may be coupled thereto. The straps in turn are tied through eyes in pair of mating Velcro strips 37 to provide for quick and easy adjustment of strap tension. The present invention also allows the use of the bridge 24 with an eye cup of modified form. In particular, FIGS. 14 and 15 illustrate protectors 40 which are identical in all respects to protectors 20, except that cups 42 are cut away in the lower center portion to provide a reading and viewing shade, so that each cup 42 can be made opaque for sunbathing and still permit the sunbather to look generally forward, or read beneath the lower edge of the cups. As before, cups 42 are connected together through removable, readily remoldable transparent bridge 24 in the same manner as hereinbefore explained, using the raised regions 31 for assembly reference.

The same parts shown in FIG. 14 may also be assembled as shown in FIGS. 11 and 12. In essence the cups 42 have been reversed, e.g., removed and swapped left for right, leaving the bridge 24 in the same position as before. With this assembly, the eye cups will now rest over the most sensitive portion of the eye, as illustrated in FIG. 13, forming a sort of mini eye protector, highly appealing to the most avid sunbathers because of its streamline quality. Thus the same parts form a sun shade and sun protector, depending on how they are assembled.

Still another form of the present improved protectors is schematically depicted in front elevation in FIG. 9, and in cross-section in FIG. 10. Thus, a portion of protectors 60 is shown, which protectors 60 comprise a pair of essentially identical eye cups 62 preferably tinted and transparent, joined to the nose bridge 24. Each eye cup 62 includes a loop 68 on the lateral surface thereof through which a head strap 70 is secured as before. A single flexible, preferably clear plastic head strap 70 may be secured to both loops 66, or a pair of head straps 70 may be secured to a strip of Velcro or the like, which can be shortened as desired.

Protectors 60 also include a strip 76 of sponge rubber, sponge plastic or other flexible resilient material secured to each cup 62 at the periphery thereof. Strips 76 cushion protectors 60 against the face and prevent wind from entering cups 62, so that protectors 60 are particularly useful for such high speed outdoor sports as skiing, ice skating, tobogganing, etc. where cold wind is an eye hazard. Venting of the eye cup may be provided, as desired, for prevention of fogging of the cups.

There has been described herein new and unique eye protectors primarily for sunbathing, and also for use as ski goggles and the like. In one form the protectors serve a substantially complete light blocking function for the eyes while still allowing tanning over the bridge of the nose, thereby finding use for sunbathing and other purposes, thereby by way of example, in optometry, or for sleepers in lighted or partially lighted rooms. By using the three piece assembly the eye cups may be decorated (plated, coated, covered with decals, etc.) in substantially any manner, while the bridge remains transparent and non-focusing. Using various partial cup forms, the same bridge may be assembled with the partial cups to provide sun shades, or mini protectors, as desired. Further, by using transparent though preferably tinted eye cups, a new and desireable form of ski goggles may be formed. (If desired the bridge and eye cups may be permanently assembled, as by glue, to avoid inadvertent disassembly say by the tension of the headband.) Therefore the net result of the present invention is a complete system of eye protection, with the various parts interfitting in various ways to provide multiple characteristics and functions. Obviously, various changes to the method of interconnecting the various parts and to the forms of partial eye cups may be made as desired. Thus, while certain preferred embodiments of the present invention has been disclosed and described herein, it will be obvious to those skilled in the art the various changes in form and detail may be made therein without departing from the spirit and scope of the invention.

What is claimed is:

1. Improved eye protectors comprising:
   a pair of eye cups, each for fitting over one eye of a user, each of said eye cups having an approximately elliptical shape and being generally complimentary to the shape of the eye to fit against the skin above and below the eye within the eye socket outline, each of said eye cups having eye cup coupling means for releasably engaging a bridge member adjacent one side thereof, and
   a bridge member for fitting over the nose bridge of a user, said bridge member being substantially transparent and shaped to avoid light focusing tendancies, and further being readily heat remoldable to conform to the desired size and shape of a user's nose bridge, said bridge member including bridge coupling means for releasably engaging each of said eye cup coupling means, said bridge coupling means and said eye cup coupling means releasably coupling in a substantially rigid manner to retain said eye cups and said bridge member in fixed relative positions.

2. The protector of claim 1 wherein said eye cups are substantially nontransmissive to light.

3. The protectors of claim 2 wherein said eye cups are opaque.

4. The protectors of claim 2 wherein said eye cups have a reflective outer surface.

5. The protectors of claim 4 wherein said eye cups have a metallic plating thereover.

6. The protectors of claim 2 wherein said eye cups cover only a part of the eye to restrict sight to the lower half of the field of vision.

7. The eye protector of claim 2 wherein said eye cups to restrict sight to the lower half of the field of vision in one orientation of the cups and wherein the cups may be detached from the bridge, rotated 180 degrees and each re-attached to the respective other side of the bridge to cover a different part of the field of vision.

8. The protectors of claim 1 wherein said cups are transparent.

9. The protectors of claim 8 wherein said cups are tinted.

10. The protector of claim 1 wherein a resilient cushion pad is disposed on the periphery of each of said cups.

11. The protectors of claim 11 wherein said eye cup coupling means comprise pockets in raised extensions of the main area of curvature of each of said cups, and wherein said bridge coupling means comprises end regions of said bridge member slideably receivable into said pockets.

12. Improved eye protectors comprising:
a pair of substantially nontransmissive eye cups, each for fitting over one eye of a user,
each of said eye cups having an approximately elliptical shape being generally complimentary to the shape of the eye to fit against the skin above and below the eyes within the eye socket outline, each of said eye cups having a socket means on its outer surface adjacent one end thereof and
a bridge member for fitting over the nose bridge of a user, said bridge member being of substantially transparent plastic and having a substantially rectangular cross-section, said bridge member having ends shaped to releasably fit with said socket means on each of said eye cups to hold them in a substantially cooperative functional disposition.

13. The protectors of claim 12 wherein said bridge is readily heat remoldable to conform to the desired size and shape of a users nose bridge.

14. The protectors of claim 12 wherein said eye cups are opaque.

15. The protectors of claim 12 wherein said eye cups have a reflective outer surface.

16. The protectors of claim 15 wherein said eye cups have a metallic plating thereover.

17. The protectors of claim 12 wherein said eye cups over the upper portion of the users eyes to form an eye shade thereover.

18. The eye protectors of claim 17 wherein said eye cups cover only a part of the eye to restrict sight to the lower half of the field of vision in one orientation of the cups and wherein the cups may be detached from the bridge, rotated 180 degrees and each re-attached to the respective other side of the bridge to cover a different part of the field of vision.

* * * * *